United States Patent
Ash et al.

(10) Patent No.: US 6,329,528 B1
(45) Date of Patent: Dec. 11, 2001

(54) PROCESS FOR PREPARING 3-(SUBSTITUTED PHENYL)-5-THIENYL OR FURYL)-1,2,4-TRIAZOLES AND NOVEL INTERMEDIATES UTILIZED THEREIN

(75) Inventors: Mary L. Ash, Zionsville; Mark W. Zettler; Norman R. Pearson, both of Carmel, all of IN (US); Duane R. Romer, Midland, MI (US); John W. Hull, Jr., Midland, MI (US); David E. Podhorez, Midland, MI (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 09/426,076

(22) Filed: Oct. 22, 1999

Related U.S. Application Data

(60) Provisional application No. 60/105,314, filed on Oct. 23, 1998.

(51) Int. Cl.[7] .................... C07D 409/04; C07D 497/04
(52) U.S. Cl. .................. 548/266.2; 544/132; 544/133; 540/603; 546/210; 546/272.4
(58) Field of Search ........................................ 548/266.2

(56) References Cited

U.S. PATENT DOCUMENTS

| | | | |
|---|---|---|---|
| 4,119,635 | 10/1978 | Omodei-Sale et al. | 260/308 R |
| 4,788,210 | 11/1988 | Luthy et al. | 514/383 |
| 5,318,959 | * 6/1994 | Ozaki, II et al. | 514/63 |
| 5,466,705 | * 11/1995 | Ozaki, I et al. | 514/383 |

FOREIGN PATENT DOCUMENTS

| | | |
|---|---|---|
| 559363 | 9/1993 | (EP) . |
| 572142 | 12/1993 | (EP) . |
| 609459 | 2/1994 | (EP) . |
| 5-310712 | 1/1993 | (JP) . |
| 9847894 | 10/1998 | (WO) . |

OTHER PUBLICATIONS

T. W. Strohmeyer et al. "New Synthesis of 2,4–Dialkyl (or diaryl)pyrazolo' 1–5a–1,3,5–traiazines" J. Heterocyclic Chemistry, 22:7–10 (1985).

M. A. Perez et al. "Regioselective Synthesis of 1,2,4–triazole and 1,2,4–oxadiazole derivatives", Synthesis, 1983:483–6 (1983).

L.L. Whitfield et al. "Heterocycles from N–Benzoylthioamides and Dinucleophilic Reagents", J. Heterocyclic Chemistry, 18: 1197 (1981).

* cited by examiner

*Primary Examiner*—Patricia L. Morris
(74) *Attorney, Agent, or Firm*—Carl D. Corvin; Donald R. Stuart

(57) ABSTRACT

New synthetic procedures for preparing insecticidal 3-(substituted phenyl)-5-(thienyl or furyl)-1,2,4-triazoles utilizing thioimidate intermediate.

7 Claims, No Drawings

PROCESS FOR PREPARING 3-(SUBSTITUTED PHENYL)-5-THIENYL OR FURYL)-1,2,4-TRIAZOLES AND NOVEL INTERMEDIATES UTILIZED THEREIN

RELATED APPLICATION

This application claims priority from U.S. Provisional Patent Application Ser. No. 60/105,314, filed Oct. 23, 1998.

FIELD OF THE INVENTION

This invention provides new synthetic procedures and intermediates for preparing insecticidal 3-(substituted phenyl)-5-thienyl or furyl)-1,2,4-triazoles.

BACKGROUND OF THE INVENTION

U.S. patent application Ser. No. 09/048,601, filed Mar. 26, 1998, incorporated herein by reference, discloses a series of highly active new insecticides. Although that patent application discloses suitable laboratory methods for preparation of the compounds, a need exists for a commercially applicable manufacturing process.

SUMMARY OF THE INVENTION

The present invention provides a process for preparing compounds of the formula (1)

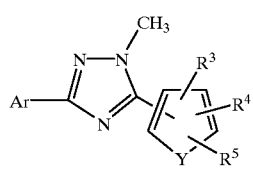

(1)

wherein
  Ar is substituted phenyl;
  Y is O or S;
  $R^3$ is selected from H, halo, lower alkyl, $(C_7-C_{21})$ straight or branched chain alkyl, hydroxy, lower alkoxy, haloalkyl, haloalkoxy, alkoxyalkyl, alkoxyalkoxy, lower alkenyl, lower alkynyl, haloalkenyl, CN, $NO_2$, $COR^6$, $CO_2R^6$, $CON(R^6)_2$, $(C_3-C_6)$ cycloalkyl, $S(O)_m R^6$, $-OSO_2R^6$, SCN, $-(CH_2)_n R^6$, $-CH=CHR^6$, $-C\equiv CR^6$, $-(CH_2)_q OR^6-(CH_2)_q SR^6$, $-(CH_2)_q NR^6R^6$, $-O(CH_2)_q R^6$, $-S(CH_2)_q R^6$, $-NR^6(CH_2)_q R^6$,

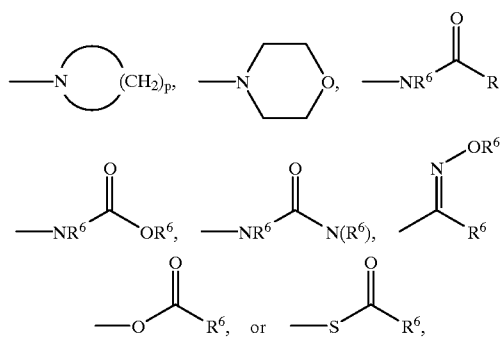

pyridyl, substituted pyridyl, isoxazolyl, substituted isoxazolyl, naphthyl, substituted naphthyl, phenyl, substituted phenyl, thienyl, substituted thienyl, pyrimidyl, substituted pyrimidyl, pyrazolyl, or substituted pyrazolyl;

$R^4$ and $R^5$ are independently H, halo, lower alkyl, lower alkoxy, haloalkyl, haloalkoxy, CN, $CO_2R^6$, $CON(R^6)_2$, or $S(O)_m$ alkyl, or if $R^4$ and $R^5$ are attached to adjacent carbon atoms, they may join to form a 5 or 6 member saturated or unsaturated carbocyclic ring which may be substituted by 1 or 2 halo, lower alkyl, lower alkoxy or haloalkyl groups;

$R^6$ is H, lower alkyl, haloalkyl, lower alkenyl, lower alkynyl, phenyl, or substituted phenyl;

m is 0, 1, or 2;
  n is 1 or 2;
  p is an integer from 2 to 6; and
  q is 0 or 1;

which comprises the steps of:

(a) reacting a compound of formula (2)

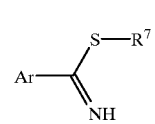

(2)

wherein Ar is as defined in formula (1) and $R^7$ is lower alkyl, or an acid addition salt thereof, with an acid chloride of the formula (3)

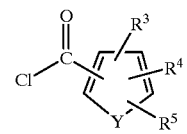

(3)

wherein Y, $R^3$, $R^4$, and $R^5$ are as defined in formula (1), in an inert organic solvent the presence of an organic or inorganic base to produce the adduct-intermediate of formula (4)

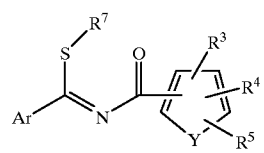

(4)

wherein Ar, Y, $R^3$, $R^4$, and $R^5$ are as defined in formula (1) and $R^7$ is lower alkyl; and (b) optionally isolating said adduct intermediate, and (c) reacting said adduct-intermediate with methyl hydrazine to produce the compound of formula (1).

Adduct-intermediates of formula (4) are novel compounds, and they are an important aspect of the invention.

Adduct-intermediates that are preferred based on desirable properties of the final products they may be used to produce are those of formula

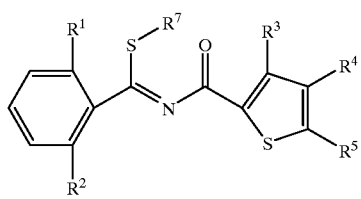

(4a)

wherein $R^1$ and $R^2$ are independently F or Cl;

$R^3$, $R^4$, and $R^5$ are independently H, $CH_3$, Cl or Br; and $R^7$ is lower alkyl.

Most preferred adduct intermediates are those of formula (4a) wherein $R^1$ is Cl, $R^2$ is F, $R^7$ is $CH_3$, and:

(a) $R^3$, $R^4$, and $R^5$ are each Cl;

(b) $R^3$ and $R^4$ are each Br and $R^5$ is H; or (c) $R^3$ is $CH_3$, $R^4$ is Cl or Br, and $R^5$ is H.

In another of its aspects, the invention provides the methyl sulfate salt of a compound of the formula

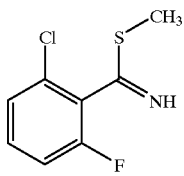

(2a)

DETAILED DESCRIPTION OF THE INVENTION

Throughout this document, all temperatures are given in degrees Celsius, and all percentages are weight percentages unless otherwise stated.

The term "lower alkyl" refers to ($C_1$–$C_6$) straight hydrocarbon chains and ($C_3$–$C_6$) branched and cyclic hydrocarbon groups.

The terms "lower alkenyl" and "lower alkynyl" refer to ($C_2$–$C_6$) straight hydrocarbon chains and ($C_3$–$C_6$) branched hydrocarbon groups containing at least one double or triple bond, respectively.

The term "lower alkoxy" refers to —O-lower alkyl.

The terms "halomethyl" and "haloalkyl" refer to methoxy and lower alkyl groups substituted with one or more halo atoms.

The terms "halomethoxy" and "haloalkoxy" refer to methyl and lower alkoxy groups substituted with one or more halo atoms.

The term "alkoxyalkyl" refers to a lower alkyl group substituted with a lower alkoxy group.

The terms "substituted naphthyl", "substituted thienyl," "substituted pyrimidyl," "substituted pyrazolyl," "substituted pyridyl," and "substituted isoxaxolyl" refer to the ring system substituted with one or more groups independently selected from halo, halo ($C_1$–$C_4$) alkyl, CN, $NO_2$, ($C_1$–$C_4$) alkyl, ($C_3$–$C_4$) branched alkyl, phenyl, ($C_1$–$C_4$) alkoxy, or halo ($C_1$–$C_4$) alkoxy.

The term "substituted phenyl" refers to a phenyl group substituted with one or more groups independently selected from halo, ($C_1$–$C_{10}$) alkyl, branched ($C_3$–$C_6$) alkyl, halo ($C_1$–$C_7$) alkyl, hydroxy ($C_1$–$C_7$) alkyl, ($C_1$–$C_7$) alkoxy, halo ($C_1$–$C_7$) alkoxy, phenoxy, phenyl, $NO_2$, OH, CN, ($C_1$–$C_4$) alkanoyl, benzoyl, ($C_1$–$C_4$) alkanoyloxy, ($C_1$–$C_4$) alkoxycarbonyl, phenoxycarbonyl, or benzoyloxy.

The term "substituted benzenesulfonyl" refers to p-chlorobenzenesulfonyl and p-toluenesulfonyl.

Unless otherwise indicated, when it is stated that a group may be substituted with one or more substituents selected from an identified class, it is intended that the substituents may be independently selected from the class.

Alkyl benzthioimidates of formula (2) are known in the literature. They are preferably used in the present invention as an acid addition salt. For example, tetrafluoroboric acid, hydrogen chloride, hydrogen bromide, hydrogen iodide, or the like, may be used. The methyl sulfate salt is preferred.

Thioimidates are readily available through alkylation of the corresponding thioamides which are themselves commercially available or can be made from the amide (*Phosphorus Sulfur* (1985), 25(3), 297–305) or nitrile (*Chem.-Ztg.* (1980), 104(12), 365–7; *J. Chem. Soc.*(1952), 742; *Can. J. Chem.* (1985), 63, 3075).

Reaction of the acid chloride (3) and the imidate (2) to give the adduct (4) can generally be accomplished in any inert solvent with any organic or inorganic base.

Reaction of compounds of formula (4) with methyl hydrazine gives the desired triazoles, generally in good yield and with a high degree of regiospecificity. An example of a previous application of a similar process is given in Synthesis, 483 (1983). In regard to regiospecificity, the undesired possible coproducts are the 5-(substituted phenyl)-3-thienyl or furyl isomers of the desired 3-(substituted phenyl)-5-thienyl or furyl-1,2,4-triazoles.

Compounds of formula (1) can also be made starting with an alkyl benzimidate, as illustrated in the following comparative example. It has been found, however, that the process of the invention, utilizing alkyl benzthioimidates, provides significantly better yields.

Comparative Example 1

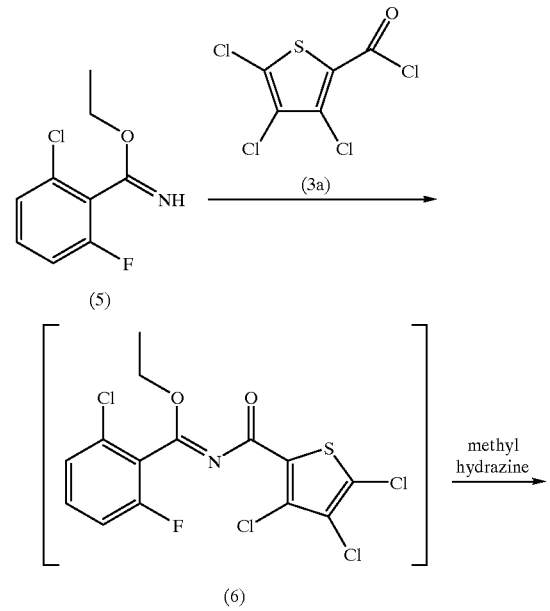

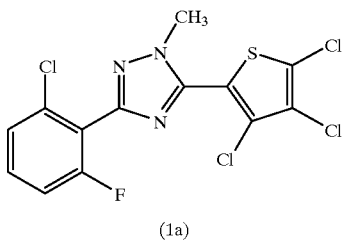

(1a)

Briefly, the reaction of ethyl 2-fluoro-6-chlorobenzimidate (5) with 3,4,5-trichloro-2-thienoyl chloride (3a) was performed in toluene using triethylamine as an acid scavenger. The presumed intermediate (6) which was not isolated, then reacted with methyl hydrazine 3 hr at reflux to give 1-methyl-3-(2-chloro-6-fluoro)phenyl-5-(3,4,5-trichloro-2-thienyl)-1H-1,2,4-triazole (1a) in 35% yield. The following paragraphs describe each step of the synthesis in greater detail.

A. 2-chloro-6-fluorobenzamide

The procedure of R. Balicki and L. Kaczmarek, *Syn. Comm.*, 23, 3149 (1993)was used. Into a 1 L round bottom flask equipped with a magnetic stirrer was added acetone (60 mL), water (60 mL), 2-chloro-6-fluorobenzonitrile (14.5 g, 93.5 mmol), urea (22.5 g, 374 mmol), 30% hydrogen peroxide (42.4 g, 374 mmol), and potassium carbonate (1.3 g, 9.0 mmol). The resulting slurry was stirred at room temperature overnight. Additional portions of urea (11.2 g, 30% hydrogen peroxide (41 g), acetone (30 mL) and potassium carbonate (0.63 g) were added and the mixture was allowed to stir for an additional 2 hr. Additional portions of urea (11.2 g, 30% hydrogen peroxide (41 g), acetone (30 mL) and potassium carbonate (0.63 g) were again added and the mixture was allowed to stir overnight. The acetone was removed in vacuo, the residue extracted with methylene chloride, the organics were combined, washed with brine, dried (MgSO$_4$) and the solvent removed in vacuo to give 15.8 g (97.5% yield) of 2-chloro-6-fluorobenzamide (97% pure by GC): mp140–141° C.; 1H NMR (CDCl3) d 7.2–7.4 (m, 2H), 7.0 (m, 1H), 6.3 (s, b, 1H), 5.9 (s, b, 1H).

B. Ethyl 2-chloro-6-fluorobenzimidate (5)

Into a 1 L round bottom flask equipped with a mechanical stirrer, thermometer, condenser, dropping funnel, under an atmosphere of nitrogen was added methylene chloride (240 mL) and 2-chloro-6-fluorobenzamide (8.65 g, 50 mmol). The temperature of the mixture was cooled to approximately 0° C. and a solution of triethyloxonium tetrafluoroborate (55 mL of 1M soln) was added dropwise at a rate such that the temperature did not rise over 0° C. The resulting mixture was allowed to warm to stir cold for 1 hr, the cooling bath was removed, the mixture was allowed to warm to RT, and was stirred at that temperature overnight. Due to incomplete conversion the mixture was cooled to 5° C. and dropwise was added and additional 11 mL of 1M soln of triethyloxonium tetrafluoroborate. The cooling bath was removed and the mixture allowed to stir for an additional 24 hr. The mixture was cooled to 0 ° C. and an additional portion of triethyloxonium tetrafluoroborate (10 mL) was added dropwise, the bath removed and the mixture stirred at RT for 19 hr. The temperature was lowered to 0° C. and a solution of potassium carbonate (50%) was added dropwise. After stirring for 15 min the layers were separated, the aqueous layer washed with methylene chloride, the organics combined, dried (Na$_2$SO$_4$), and the solvent removed in vacuo to give an oil: ethyl 2-chloro-6-fluorobenzimidate (94%), starting material (5%). This material was used without further purification.

C. Preparation of 1-methyl-3-(2-chloro-6-fluoro) phenyl-5-(3,4,5-trichloro-2-thienyl)-1H-1,2,4-triazole(1a) from ethyl 2-chloro-6-fluorobenzimidate (5)

Into 50 mL one necked round bottom flask equipped with a magnetic stirrer and condenser under an atmosphere of nitrogen was added 3,4,5-trichloro-2-thienyl carboxylic acid (0.69 g, 3 mmol), EDC (20 mL), thionyl chloride (0.53 g, 0.32 mL, 4.5 mmol) and several drops of DMF. The mixture was allowed to reflux for 3 hr and the solvent was removed in vacuo to a constant weight. To a three necked flask equipped with a condenser and containing ethyl 2-chloro-6-fluorobenzimidate (94% pure, 0.60 g, 3.0 mmol), and triethylamine (0.10 g, 0.14 mL, 6.0 mmol), and toluene (10 mL) was added dropwise 3,4,5-trichloro-2-thienoyl chloride dissolved in toluene (10 mL). The temperature of the mixture was brought to the point of reflux and maintained at that temperature for 3 hr. To the refluxing mixture was added methyl hydrazine (0.86 g, 1.0 mL, 9 mmol) dissolved in toluene was added dropwise. The mixture was allowed to reflux for 1 hr. The toluene was removed in vacuo and the residue was purified via column chromatography to give 1-methyl-3-(2-chloro-6-fluoro)phenyl-5-(3,4,5-trichloro-2-thienyl)-1H-1,2,4-triazole (1a): 0.42 g (35% yield), GC[Mez80] at 19.1 min, mass 395/397/399.

EXAMPLE 1

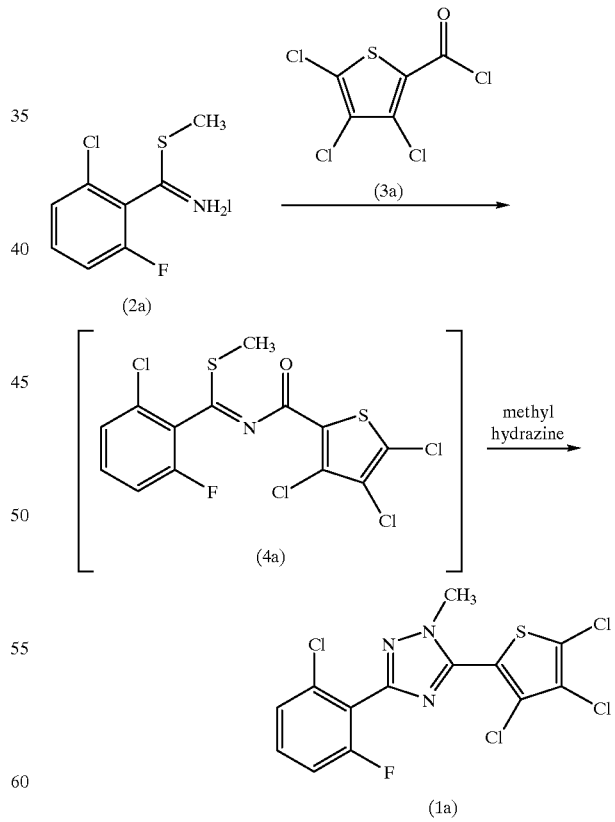

Briefly, the reaction of methyl 2-fluoro-6-chlorobenzthioimidate hydroiodide (2a) with 3,4,5-trichloro-2-thienoyl chloride (3a) was performed in toluene using triethylamine as an acid scavenger. The presumed intermediate (4a) which was not isolated, then reacted with methyl hydrazine for 3 hr at reflux to give 1-methyl-3-(2-chloro-6-fluoro)phenyl-5-(3,4,5-trichloro-2-thienyl)-1H-1,2,4-triazole(1a) in 78% yield.

The following paragraphs describe each step of the synthesis in greater detail.

A. Preparation of 2-chloro-6-fluorobenzthioamide

Into a 250-mL three necked round bottom flask equipped with a mechanical stirrer, dry ice condenser, dropping funnel, and outlet to a trap filled with bleach was added pyridine (45 mL), 2-chloro-6-fluorobenzonitrile (15.5 g, 0.1 mol), triethylamine (13.4 g, 18.6 mL, 0.133 mol), and sodium sulfide hydrate (36.0 g, 0.15 mol). The temperature of the resulting solution was lowered to approximately 5° C. using an ice bath. To the stirred slurry was added dropwise concentrated hydrochloric acid (25.8 g, 0.266 mol). The rate of addition of the hydrochloric acid was such that the temperature of the reaction mixture did not exceed 25° C. with an addition time of 20 min. The cooling bath was removed and the slurry was allowed to warm to RT and to stir over night. An additional 40 grams of sodium sulfide and 50 mL of hydrochloric acid was added to the mixture and allowed to stir over night. An additional 40 grams of sodium sulfide and 50 mL of hydrochloric acid was added and the mixture allowed to stir over the weekend. The mixture was poured into water (2 L) and was extracted with ether. The ether layer was washed with dilute sulfuric acid, water, brine, dried ($MgSO_4$), and the solvent removed in vacuo to give 16.1 g of crude product which was recrystallized from ethyl acetate to give 2-chloro-6-fluoro-benzthioamide as light yellow crystals: mp 156–158° C.

B. Preparation of methyl 2-chloro-6-fluorobenzthioimidate hydrolodide (2a)

Into a 50 mL three necked round bottom flask equipped with a magnetic stirrer was added 2-chloro-6-fluorobenzthioamide (3.78 g, 20 mmol) and acetone (20 mL). Dropwise was added iodomethane (2.84 g, 1.24 mL, 20 mmol) and the mixture was allowed to stir at room temperature overnight with monitoring via HPCL (60/40 acetonitrile/water). The solids were removed via filtration and washed with small portions of acetone to give methyl 2-chloro-6-fluorobenzthioimidate hydroiodide as a light yellow solid: 3.1 g (46.9% yield): $^1$H NMR (DMSO-$d_6$) δ7.7 (m, 1H), 7.5 (m, 2H), 2.7 (s, 3H).

C. Preparation of 1-methyl-3-(2-chloro-6-fluoro)phenyl-5-(3,4,5-trichloro-2-thienyl)-1H-1,2,4-triazole (1a) from 2-chloro-6-fluorobenzthioimidate hydroiodide (2a)

Into 50 mL one necked round bottom flask equipped with a magnetic stirrer and condenser under an atmosphere of nitrogen was added 3,4,5-trichloro-2-thienyl carboxylic acid (0.69 g, 3 mmol), EDC (20 mL), thionyl chloride (0.53 g, 0.32 mL, 4.5 mmol) and several drops of DMF. The mixture was allowed to reflux for 3 hr and the solvent was removed in vacuo to a constant weight. To a three necked flask equipped with a condenser and containing methyl 2-chloro-6-fluorobenzthioimidate hydroiodide (0.99 g, 3.0 mmol), and triethylamine (0.20 g, 0.28 mL, 12 mmol), and toluene (20 mL) was added dropwise 3,4,5-trichloro-2-thienoyl chloride dissolved in toluene (10 mL). The mixture was brought to the point of reflux and maintained at that temperature for 3 hr. To the refluxing mixture was added methyl hydrazine (0.86 g, 1.0 mL, 18 mmol) dissolved in toluene was added dropwise. The mixture was allowed to reflux for 1 hr, the toluene was removed in vacuo, and the residue chromatographed on silica gel to give 0.87 g (73% yield), GC[Mez80] at 19.1 min, mass 395/397/399.

Thus, the process of the invention provided a significantly better yield (73% versus 35%)than the process using an alkyl benzimidate in place of the alkyl benzthioimidate required by the invention.

The preferred process for preparing the methyl 2-chloro-6-fluorobenzthioimidate produces the methyl sulfate salt.

EXAMPLE 2

Preparation of methyl 2-chloro-6-fluorobenzthioimidate using dimethylsulfate

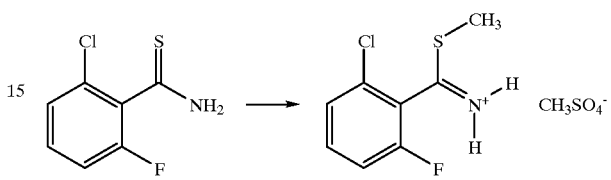

Into a 25-mL three-necked round bottom flask equipped with a magnetic stirrer was added 2-chloro-6-fluorobenzthioamide (1.89 g, 10.0 mmol) and toluene (10 mL). Dimethylsulfate was added dropwise and the mixture was allowed to stir at reflux using a Dean Stark trap. The solids were removed via filtration and washed with small portions of toluene to give methyl 2-chloro-6-fluorobenzthioimidate as a light yellow solid: 2.7 g (87% yield): $^1$H NMR (DMSO-$d_6$) δ7.7 (m, 1H), 7.5 (m, 2H), 3.3 (s, 3H), 2.7 (s, 3H); 98% pure by HPLC analysis.

Comparing the results of Example 2 with those of Example 1C, it is clear that Example 2 is a significant improvement. Example 2 is higher yielding (87% versus 46%), yields a purer product (98% versus 96%) and uses a reagent, dimethyl sulfate, that is much cheaper both in terms of initial cost and disposal issues.

The following example illustrates the complete process incorporating use of the methyl sulfate salt and isolation of the adduct intermediate.

EXAMPLE 3

A. 2-Chloro-6-Fluorobenzthioamide

2-Chloro-6-fluorobenzonitrile, (99.1%, 62.2 g, 0.40 mol) was weighed into a 1-L three-necked roundbottom flask equipped with a condenser and an overhead electric stirrer, along with $Et_3N$ (78 mL, 56.6 g, 0.56 mol) and 180 mL (176.04 g, 2.23 mol) of pyridine. The reactor was purged with a slow stream of $N_2$ and vented to a 13% bleach solution. The stirring solution was cooled to −19° C. in a $CCl_4$/dry ice bath, and $H_2S$ gas (33.6 g, 0.99 mol) was sparged below the liquid surface at a rate of 0.4 g/min over a period of 82 min. During the gas addition, the solution temperature rose to −11° C. The yellow-green solution was allowed to gradually warm to 25° C. and stir overnight with a slow $N_2$ purge of the reactor head space into bleach solution. The solution was poured into 1.6 L of ice water, stirred, and the resulting white crystals were collected on a buchner funnel and rinsed with additional water. After 2 h of air drying, the moist filter cake was vacuum oven dried for 5 h at 65° C. to give 54.5 g of 2-Chloro-6-Fluorobenzthioamide (72% wt. % yield), mp 155–160° C., having a GC area % purity of 98.8% and containing 1.2% 2-Chloro-6-fluorobenzonitrile.

B. Methyl 2-chloro-6-fluorobenzthioimidate methyl sulfate salt

2-Chloro-6-fluorobenzthioamide (21.9 g, 0.12 mol) and dimethyl sulfate (12 mL, 16.0 g, 0.13 mol) were stirred together in 100 mL of toluene and refluxed for 2 h. The slurry was cooled to 25° C. and the white crystals collected on a glass buchner funnel and rinsed with a small quantity of acetone. After air suction drying for 1 h, 35.5 g of methyl 2-chloro-6-fluorobenzthioimidate methylsulfate salt was obtained, mp 147–151° C., representing a nominal wt. % yield of 96%.

A sample of this salt was recrystallized from cold isopropanol followed by vacuum oven drying at 75° C. to give white crystals, mp 152–157° C. Elemental analysis results are summarized in the table below.

|   | Theoretical | Found |
|---|---|---|
| C | 34.23% | 34.47% |
| H | 3.51% | 3.61% |
| N | 4.44% | 4.45% |
| Cl | 11.23% | 11.27% |
| S | 20.31% | 20.16% |

C. Methyl-2-chloro-6-fluoro-N-[(3,4,5-trichloro-2-thiophene)carbonyl]-benzenecarboximidothioate

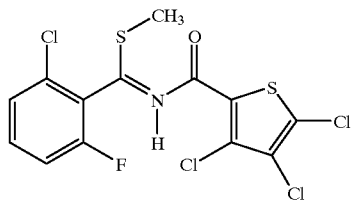

2-Chloro-6-fluorobenzthioimidate methylsulfate salt (35.5 g, 0.11 mol) and 155 mL of toluene were placed into a 1 L three-necked roundbottom flask with a bottom drain and overhead stirrer. The solution was cooled with an ice bath, and to this slurry was added triethylamine (32 mL, 23.2 g, 0.23 mol). A mild exotherm was noted. A solution of 3,4,5-trichloro-2-thiophenecarbonyl chloride (30.69 g, 0.12 mol) was added dropwise over 30 min at 0° C. After 1 h of cooling, the ice bath was removed and the mixture was stirred at 25° C. for 3 days. The solution was washed with two 250 mL portions of water, and the toluene was evaporated to give 41.3 g of tan solid. This solid was washed with $CH_3CN$, filtered and dried to give 32.8 g of white solid, m.p. 124–126° C., for a weight % yield of 70.2%.

A purified sample of the adduct was obtained by recrystallization from warm $CH_3CN$ followed by vacuum oven drying at 60° C. for 3 h; m.p. 125–128° C. Elemental analysis results are summarized in the table below.

|   | Theoretical | Found |
|---|---|---|
| C | 37.43% | 37.18% |
| H | 1.45% | 1.43% |
| N | 3.36% | 3.62% |
| Cl | 34.00% | 34.08% |
| F | 4.55% | 5.30% |
| S | 15.37% | 15.64% |

D. 1-Methyl-3-(2-chloro-6-fluoro)phenyl-5-(3,4,5-trichloro-2-thienyl)-1H-1,2,4-triazole The adduct intermediate of part C (6.1 g, 0.0146 mol) and 75 mL toluene were placed into a 250 mL three-necked flask and brought to reflux. Methylhydrazine (1.6 mL, 1.39 g, 0.0301 mol) as a solution in 25 mL of toluene was added dropwise to the refluxing solution over a period of 1 h. The solution was refluxed for an additional 2 h, then was cooled to 25° C., washed with aqueous $Na_2CO_3$, then water, and the organic phase was evaporated to give a viscous oily residue. The ratio of regio isomers by GC area % analysis was 13.7/1 in favor of the desired isomer. The oily residue was triturated with a small volume of $CH_3CN$, cooled to 0° C. in a freezer for 1 h, and the resulting white crystals were collected on a buchner funnel and air-suction dried to give 4.1 g (70%) of the desired product, m.p. 128–130.5° C., with a GC area % purity of 98.3% and containing 1.4% of a regio isomer impurity.

A preferred synthetic method is illustrated in the following Scheme I:

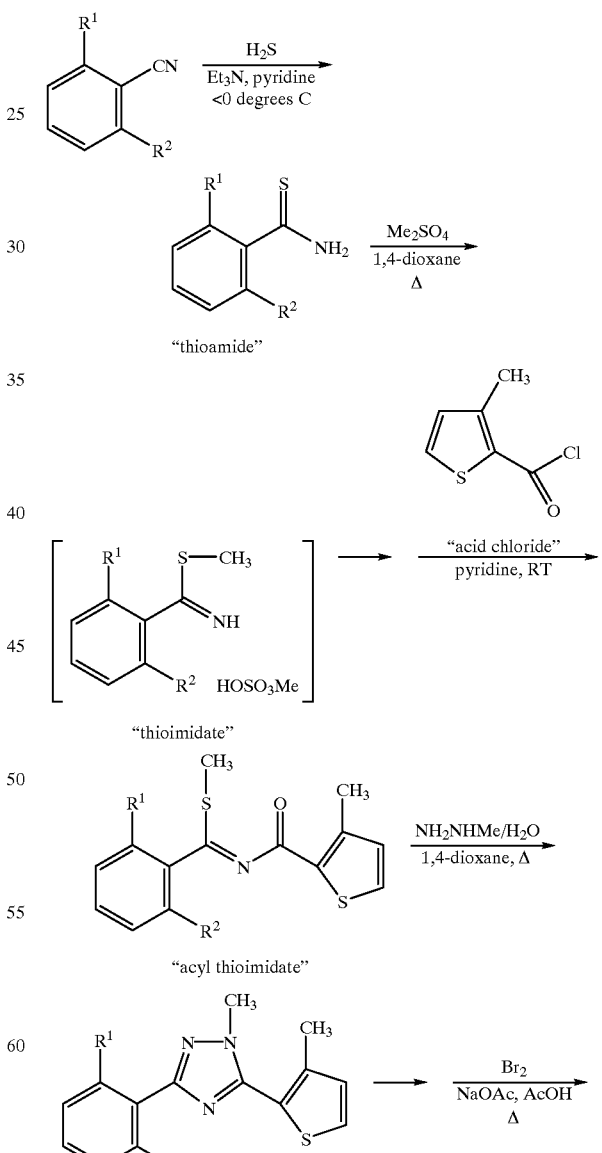

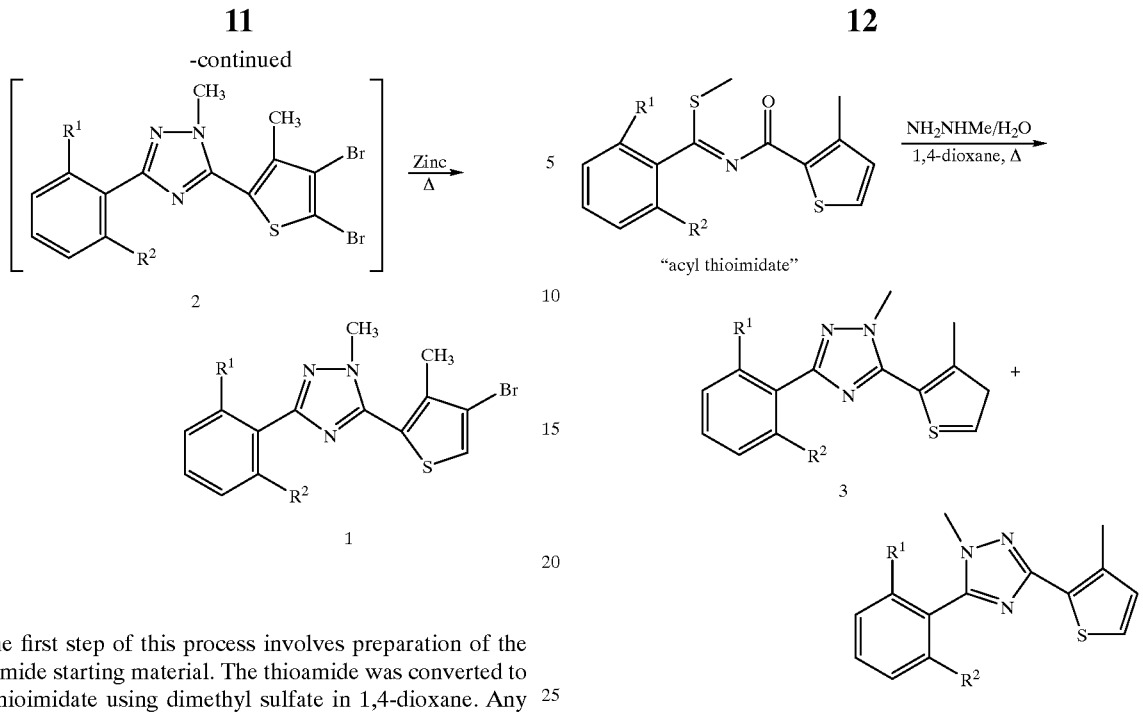

The first step of this process involves preparation of the thioamide starting material. The thioamide was converted to the thioimidate using dimethyl sulfate in 1,4-dioxane. Any known imidate forming procedure known in the literature can be used for this transformation. Common methylating agents such as methyliodide, methylbromide and dimethyl sulfate can be used. Any common solvent compatible with the reaction conditions can be used, with toluene, acetonitrile, 1,4-dioxane, THF, and 1,2-dichloroethane most convenient. Reaction temperatures range from RT to the reflux temperature of the solvent. The thioimidate can be isolated as its salt or used directly without isolation in the next transformation.

The thioimidate was next acylated with 3-methyl-2-thiophenecarbonyl chloride ("acid chloride") to give the acyl thioimidate adduct. Any known acylation conditions can be used for this transformation. Any common organic and inorganic base can be used, with $Na_2CO_3$, $NaHCO_3$, pyridine and triethylamine most convenient. Solvents preferred include 1,4-dioxane, THF, dichloromethane, and 1,2-dichloroethane, but any solvent compatible with the reaction conditions can be used. Reaction temperatures in the 0° to 60° C. range are suitable, with temperatures near RT most convenient. The acyl thioimidate was isolated by dilution of the reaction mixture with water and filtration followed by air drying. This acyl thioimidate was of sufficient purity to be used directly in the following cyclization step.

The acyl thioimidate was cyclized to the 1,2,4-triazole ring system by treatment with methylhydrazine. The methylhydrazine could be added neat or as a solution in a compatible solvent such as water. Any solvent compatible with the reaction conditions can be used, with toluene, 1,4-dioxane, THF, and short chain alcohols preferred. The methylhydrazine can be added all at once to the reaction mixture, or added in portions over a 1 hour time period. The cyclization can be carried out in the temperature range of RT to reflux temperature of the solvent being used. Ratios of the intermediate 3 to its off-isomer 4 range from 6:1 to 40:1 depending upon the reaction conditions used.

It was found most convenient to use 1,4-dioxane at a cyclization temperature of 80° C. to give a 30:1 ratio of isomers. Workup consisted of removal of the solvent followed by crystallization from a suitable solvent such as 95% EtOH. Alternately, the reaction mixture could be diluted with water and filtered to provide the intermediate 3. Air drying provided product of sufficient purity for the next bromination step.

The last two steps illustrated in Scheme I are the bromination of triazole 3 to give the dibromo intermediate 2, followed by removal of one of the bromine atoms. Any standard brominating reagent known in the literature can be used, with $Br_2$ being the most convenient. Two to five molar equivalents of $Br_2$ can be used at temperatures from 25° to reflux temperature of the solvent. Time of reaction range from 1 hour to 24 hours. Any solvent compatible with bromination conditions can be used such as 1,4-dioxane, 1,2-dichloroethane, and acetic acid. The generated HBr can be neutralized by running the reaction in the presence of a proton acceptor such as sodium acetate. It was found most convenient to run the reaction in acetic acid with sodium acetate using four equivalents of $Br_2$.

The dibromo analogue 2 can be isolated or one may proceed directly into the next chemical transformation, if desired, without isolation. In the last step, zinc dust is added to the reaction mixture to reduce off the 5-bromine on the thiophene ring. Any known methods of aromatic halogen reduction could be used, but zinc dust was found most convenient. Two to three equivalents of zinc can be used; the extra molar equivalents were needed to reduce unreacted $Br_2$. The temperature of the reduction ranged from 25° to 90° C. This reduction is highly selective and leaves the 4-bromine of the thiophene ring unaffected. The product is conveniently isolated by dilution of the reaction mixture with water followed by filtration.

Another preferred synthetic method is illustrated in the following Scheme II:

Scheme II

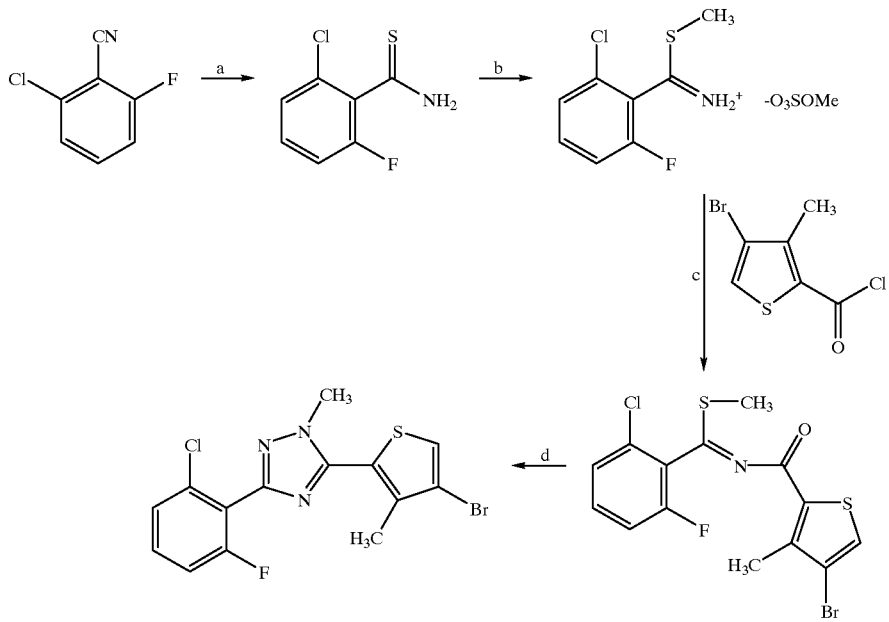

Conditions for each step in Scheme II are as follows: a) H₂S/Et₃N/Pyridine, −20° C., b) (CH₃O)₂SO₂, 1,4-dioxane, 80° C., c) pyridine, 4-bromo-TAC, 30° C., d) MeNHNH₂/H₂O, 1,4-Dioxane, 80° C.

The 4-bromo-3-methyl-2-thiophenecarbonyl chloride used in step c of Scheme I can be prepared using the procedure illustrated in Scheme III:

convenient are methyl or ethyl esters of 3-methyl-2-thiophenecarboxylic acid.

One aspect of the invention is a novel preparation of ethyl-3-methyl-2-thiophenecarboxylate via a palladium-catalyzed carboxylation of 2-bromo-3-methylthiophene.

Methyl 3-methyl-2-thiophenecarboxylate may be prepared by a Grignard reaction of 2-bromo-3-methylthiophene

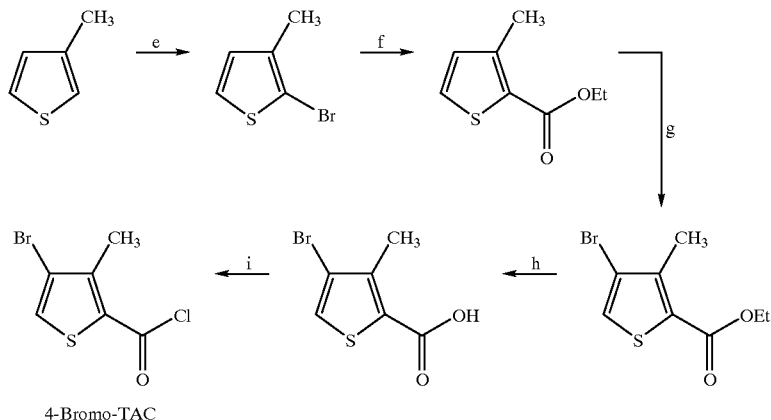

4-Bromo-TAC

Conditions for each step in Scheme III are as follows: e) Br₂/succinimide, f) 10% Pd/C, DPPP, 0.2 mol %, CO pressure, EtOH, NaOAc, g) i) 2 Br₂/2 NaOAc/HOAc, 80° C., ii) Zn dust, HOAc/H₂O, h) NaOH/H₂O, i) SOCl₂/DMF, 1,2-DCE.

Scheme III illustrates use of ethyl 3-methyl-2-thiophenecarboxylate as the intermediate utilized in step g, but any short chain alkylester of 3-methyl-2-thiophenecarboxylic acid may be used. These include, but are not limited to, methyl, ethyl, propyl or butyl. Most with dimethylcarbonate. Either the methyl or ethyl ester of 3-methyl-2-thiophene carboxylic acid may be prepared by Fisher esterification with the appropriate alcohol, or by reaction of 3-methyl-2-thiophenecarboxylic acid chloride with the appropriate alcohol.

Yet another preferred embodiment is illustrated in Scheme IV:

Scheme IV

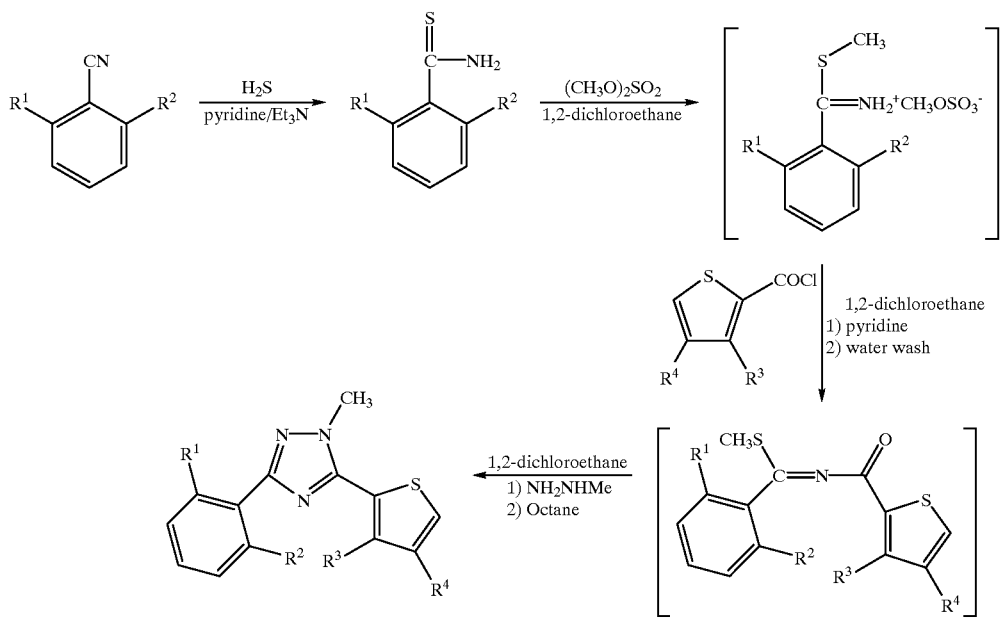

Noteworthy features of the embodiment illustrated in Scheme IV include:
1) the methyl sulfate salt of the benzthioimide is used;
2) 1,2-dichloroethane is used as the solvent in each step;
3) the synthesis is carried out in one pot, without isolation of intermediates;
4) octane is added in the final step to promote crystallization of the product.

The individual steps in the Scheme IV are described in detail hereafter:

The first step of this process involves the conversion of 2-chloro-6-fluorobenzonitrile to the thioamide. Any of the methods known in the chemical literature can be used for this thioamide formation reaction. Sodium sulfide can be used as the sulfur source, but it has been found most convenient to use hydrogen sulfide gas. Reaction temperatures used are in the −35° to 50° C. range, with −10° to RT most convenient. Any common solvent compatible with the reaction conditions can be used. Pyridine and ethanol are suitable. Any common amine base, for example triethylamine, can be used.

The next three distinct chemical transformations are most conveniently carried out in one process step, without isolation of two intermediates. The two intermediates can be isolated and characterized if desired. In the first transformation, the 2-chloro-6-fluorothiobenzamide is converted to the methyl thioimidate. Any known imidate forming procedure known in the literature can be used for this transformation. Common methylating agents such as methyliodide, methylbromide and dimethyl sulfate can be used. Any common solvent compatible with the reaction conditions can be used, with toluene, acetonitrile, THF, and 1,2-dichloroethane most convenient. Reaction temperatures range from RT to the reflux temperature of the solvent. The thioimidate can be isolated as its salt or used directly without isolation in the next transformation.

The thioimidate is next acylated with 3,4,5-trichloro-2-thiophenecarbonyl chloride to give the acylated adduct. This adduct can be isolated and characterized if desired, but was found to be most conveniently used directly without isolation. Any known acylation conditions can be used for this transformation. Any common organic and inorganic base can be used, with $Na_2CO_3$, $NaHCO_3$, pyridine and triethylamine most convenient. Solvents preferred include THF, dichloromethane, and 1,2-dichloroethane, but any solvent compatible with the reaction conditions can be used. Reaction temperatures in the 0° to 60° C. range are suitable, with temperatures near RT most convenient.

The acylated adduct is finally cyclized to the 1,2,4-triazole ring system by treatment with methylhydrazine. A two step procedure using hydrazine to give the unsubstituted triazole followed by methylation could be used, but it is convenient to use methylhydrazine directly. The methylhydrazine can be added neat or as a solution in a compatible solvent such as water. Any solvent compatible with the reaction conditions can be used, with toluene, THF, and 1,2-dichloroethane preferred. The methylhydrazine can be added all at once to the reaction mixture, or added in portions over a 1 hour time period. The cyclization can be carried out in the temperature range of RT to reflux temperature of the solvent being used. Ratios of the desired product to its off-isomer range from 1:4 to 50:1 depending upon the reaction conditions used. It is most convenient to use 1,2-dichloroethane at a cyclization temperature of 70° C. to give a 38:1 ratio of 1-methyl-3-(2-chloro-6-fluoro)phenyl-5-(3,4,5-trichloro-2-thienyl)-1H-1,2,4-triazole to its "off isomer."

EXAMPLE 4

This example illustrates the process of Scheme IV.

A. Preparation of 2-chloro-6-fluorobenzthioamide in pyridine/triethylamine solvent 2-Chloro-6-fluorobenzonitrile, (99.1%, 62.2 g, 0.40 mol) was weighed into a 1-L three-necked roundbottom flask equipped with a condenser and an overhead electric stirrer, along with $Et_3N$ (78 mL, 56.6 g, 0.56 mol) and 180 mL (176.04 g, 2.23 mol) of pyridine. The reactor was purged with a slow stream of $N_2$ and vented to a 13% bleach solution. The stirring solution was cooled to −19° C. in a CCl$_4$/dry ice bath, and H$_2$S gas (33.6 g, 0.99 mol) was sparged below the liquid surface at a rate of 0.4 g/min over a period of 82 min. During the gas addition, the solution temperature rose to −11° C. The yellow-green solution was allowed to gradually warm to 25° C. and stir overnight with a slow N$_2$ purge of the reactor head space into bleach solution. The solution was poured into 1.6 L of ice water, stirred, and the resulting white crystals were collected on a buchner funnel and rinsed with additional water. After 2 h of air drying, the moist filter cake was vacuum oven dried for 5 h at 65° C. to give 54.5 g of 2-Chloro-6-Fluorobenzthioamide (72% wt. % yield), mp 155–160° C., having a GC area % purity of 98.8% and containing 1.2% 2-Chloro-6-fluorobenzonitrile.

B. Preparation of 2-chloro-6-fluorobenzthioamide in ethanol/triethylamine solvent 2-Chloro-6-fluorobenzonitrile, (99.1%, 15.2 g, 0.10 mol) was weighed into a 1-L three-necked roundbottom flask equipped with a condenser and an overhead electric stirrer, along with Et$_3$N (41 mL, 29.8 g, 0.29 mol) and 54 mL of 95% ethanol. The solution was cooled to 0° C. with an ice bath and H$_2$S gas (13.5 g, 0.40 mol) was sparged below the liquid surface at a rate of 0.2 g/min over a period of 70 min. The ice bath cooling was continued for 2 h, then the flask was allowed to gradually warm to room temperature. The yellow solution was poured into 426 g of stirring ice water in a 1 L Erlenmeyer flask, and the resulting white solid was collected on a buchner funnel and rinsed with additional water. This filter cake was dissolved in 1,2-dichloroethane and evaporated to dryness on a rotary evaporator (67° C. bath) to ensure dryness, giving 13.42 g (72% weight % yield) of the thioamide as a white solid.

C. 3,4,5-Trichloro-2-thiophenecarbonyl chloride

A mixture of 20.4 g (0.088 mole) of 3,4,5-trichloro-2-thiophenecarboxylic acid, 7.3 mL (0.1 mole) of thionyl chloride, 0.2 mL of DMF and 80 mL of 1,2-dichloroethane was heated at reflux temperature for 3 h. The reaction mixture became a clear solution after 1 h of heating. The mixture was allowed to cool to RT, concentrated in vacuo and exposed to high vacuum to give 22.0 g (>98% wt) an oil which solidified upon standing to an off-white powder, mp 37°–41° C.

D. 1-Methyl-3-(2-chloro-6-fluorophenyl)-5-(3,4,5-trichloro-2-thienyl)-1H-1,2,4-triazole A mixture of 94.82 g (0.5 mole) of 2-chloro-6-fluorobenzthioamide, 50 mL (0.525 mole) of dimethyl sulfate, and 800 mL of 1,2-dichloroethane was heated at reflux temperature for 1 h. LC analysis indicated complete conversion to the thioimidate. The reaction solution was cooled to RT with ice-bath cooling, and the thioimidate salt precipitated from the solution. To the thick slurry was added 100 mL (1.25 mole) of pyridine. The salts instantly dissolved into solution, followed by immediate precipitation of pyridine salts. After further cooling to 10° C., 125 g (0.5 mole) of 3,4,5-trichloro-2-thiophenecarbonyl chloride dissolved in 200 mL of 1,2-dichloroethane was added in three portions. Temperature of the reaction mixture rose to 20° C. during each addition and was allowed to cool back to 10° C. before the next addition. The reaction mixture was allowed to stir at RT for 0.5 h. LC analysis indicated major acylated thioimidate and <2% area of starting thioimidate. To the slurry was added 1.0 L of water and the layers separated. LC internal standard analysis of the organics indicated a 94% in-pot yield of the acylated intermediate. The 1,2-dichloroethane solution was heated to 70° C., and a solution of 40 mL (0.75 mole) of methylhydrazine in 60 mL of water was added via a pump over 20 min. The temperature of the reaction mixture was maintained between 70° and 73° C. The solution was heated an additional 2 h, when GC analysis indicate no remaining acylated intermediate and a 38:1 ratio of desired product/off-isomer. The reaction mixture was cooled to RT, and 500 mL of octane followed by 1 L of 0.5 N LiOH was added. After stirring for 10 min, the layers were separated. The organic solution was then stirred with 750 mL of a 2% bleach solution for 0.25 h to remove remaining mercaptan compounds. The temperature of the mixture rose to 31° C. during this reaction. The layers were separated and upon concentration of the 1,2-dichloroethane on a rotoevaporator, a tan sandy precipitate formed. This solid was filtered and exposed to vacuum oven drying at 40° C. to give 144.8 g (73% wt) of the desired product as a tan crystalline powder. GC analysis indicated <0.2% area of the off-isomer, and LC internal standard analysis indicated a 98% purity, giving an overall isolated 72% yield of 1-methyl-3-(2-chloro-6-fluoro)phenyl-5-(3,4,5-trichloro-2-thienyl)-1H-1,2,4-triazole.

EXAMPLE 5

3-(2-Chloro-6-fluorophenyl)-1-methyl-5-(3-methyl-4-bromo-2-thienyl)-1H-1,2,4-triazole This example illustrates the process of Scheme I.

A. 2-Chloro-6-fluorobenzenecarbothioamide

2-Chloro-6-fluorobenzonitrile (1230 g, 7.91 mol) was weighed into a 22 L jacketed glass reactor (without bottom drain), along with Et$_3$N (1.5 L, 10.76 mol) and pyridine (2.4 L, 29.67 mol) and the stirring solution was cooled to −18° C. under a blanket of N$_2$. The reactor N$_2$ purge mineral oil bubbler was vented to a carboy containing 16 L of 12% bleach solution. Hydrogen sulfide gas (407 g, 11.94 mol) was introduced below the surface of the cold reactor solution over a period of 5.5 hrs. During this time the reactor temperature rose from −18 to −4° C. The solution was stirred overnight at −7° C. (16 hrs), sampled by GC to ensure complete conversion of 2,6-CFBN, then quenched by vacuum transfer of the reactor solution into a second 22 L flask containing 14 L of cold water stirring at 300 RPM (Note: Quenching into a well-stirred tank of cold water produces small white particles of easily filtered product). After the vacuum transfer was completed, another 2 L of cold water was added to the stirring slurry. The light yellow slurry of white solid was drained from the quench tank into bottles, and the solid product was collected by filtration through a course glass buchner funnel, followed by washing of the solid product with an excess of de ionized water. The white solid was air suction dried for 3 h, air dried in a glass pan overnight, then dried in a vacuum oven at 50° C. at 0.3 mm Hg for 8 hrs to give 1004 g (67%) of dry 2-chloro-6-fluorobenzenecarbothioamide, m.p. 153–157° C.

B. Methyl 2-chloro-6 fluoro-N-[(3-methyl-2-thiophene)carbonyl]benzenecarboximidothioate To a 22 L jacketed glass reactor under a N$_2$ purge was added 6 L of 1,4-dioxane via a pump. After the mechanical stirrer had been started, 1140 g (6.0 mol) of 2-chloro-6 fluorobenzenecarbothioamide was added to the reactor, followed by 630 mL (6.65 mol) of dimethyl sulfate. The reaction mixture was heated to 80° C. for 1.5 h. During the course of heating, the reaction mixture became a solution near 55° C., with a precipitate reforming as the reaction proceeded. LC analysis indicated <2% area starting thioamide and 96% area methyl 2-chloro-6-fluorobenzenecarboximidothioate methylsulfonate salt ("thioimidate"). The reaction mixture was cooled to 30° C., and 1.2 L (15 mol) of pyridine was added. When the reaction temperature had fallen back below 30° C., 970 g (6.04 mole) of 3-methyl-2-thiophenecarbonyl chloride ("acid chloride") was added via a PE dropping funnel over 20 min. An exotherm of seven degrees was observed during this addition. After stirring at room temperature for 1 h, LC analysis indicated <3% area of the thioimidate and 93% area acyl thioimidate. To the reaction mixture was added 9 L of water, and the mixture stirred at room temperature for 1 h. The mixture was filtered through a crock filter with vacuum removal of the mother liquor into a second 22 L glass reactor. The white solid was air dried in a glass pan overnight to give 2000 g of a white powder, 98% LC area. This material was used directly in the next step without further purification.

C. 3-(2-Chloro-6-fluorophenyl)-1-methyl-5-(3-methyl-2-thienyl)-1H-1,2,4-triazole To a 22 L jacketed glass reactor under a $N_2$ purge was added 9 L of 1,4-dioxane via a pump. The $N_2$ purge outlet was connected to a carboy containing 12 L of fresh 12% wt bleach solution. To the stirred dioxane was added 1970 g (6 mol) of methyl 2-chloro-6 fluoro-N-[(3-methyl-2-thiophene)carbonyl]benzenecarboximido-thioate and the mixture heated to 80° C. During heating the mixture became a clear solution. Upon reaching 80° C., a solution of 400 mL (7.5 mol) of methylhydrazine in 600 mL of water was added over 20 min via a pump. The mixture was heated near 80° C. for 3.5 h, when GC area analysis indicated 2% starting acyl thioimidate, 94% desired product, and 3% off-isomer 4. The reaction mixture was cooled to 30° C. and vacuum transferred to a roto-evaporator connected to bleach trapping. The reaction mixture was concentrated to an amber oil, dissolved in 800 mL of 95% EtOH, and transferred to a 4 L Erlynmeyer flask. The solution was scratched and seeded with the title compound and allowed to crystallize in a refrigerator overnight. After filtration the precipitate was air dried in a glass pan overnight to give 1376 g of an off-white powder, 99% area GC. This material was used directly in the next step without further purification.

D. 3-(2-Chloro-6-fluorophenyl)-1-methyl-5-(3-methyl-4-bromo-2-thienyl)-1H-1,2,4-triazole The triazole 3-(2-Chloro-6-fluorophenyl)-1-methyl-5-(3-methyl-2-thienyl)-1H-1,2,4-triazole (1715 g, 5.57 mol) and anhydrous sodium acetate (1830 g, 22.3 mol) were weighed as solids into a 22 L jacketed glass reactor under a slow $N_2$ purge, followed by 8.5 L glacial AcOH. Heating of the mixture was begun, and at 66° C. a solution of $Br_2$ (1.15 L, 22.3 mol) in 2.5 L glacial AcOH was added by peristaltic pump over a period of 40 min., at a rate to keep the reaction temperature below 85° C. During heat up most of the solids dissolve. The stirring red solution was heated 1 h at 80° C. and then a sample was removed and analyzed by GC to verify >99% conversion to the dibromo intermediate. Cooling was placed on the jacket, and 1695 g ice was added to the solution, which dropped the temperature from 70° C. to 50° C. At 38° C. zinc powder (815 g, 12.5 mol) was added in 55 g shots over a period of 40 min to dispel excess $Br_2$. During this addition the reactor temperature rose to 71° C. Additional zinc powder (650 g, 9.9 mol) was then added in 50 g shots over a period of 50 min with a stream of $N_2$ passing through the reactor to dispel $H_2$ gas safely. During the addition of this second portion of zinc powder, jacket heating (85° C.) was applied to bring the reaction mixture to 78° C. (Note: zinc addition at this point leads to $H_2$ gas evolution and should be done at such a rate as to control the rate of evolution and maintain precautions against flammability and explosion hazards). After zinc addition was completed, the reactor was stirred at 78° C. for 15 min, then was sampled for GC analysis (Note: the reactor can be maintained at this point at 80° C. overnight to keep the product dissolved if insufficient time exists to carry out the filtration). The solution was filtered warm through a layer of celite on a course glass buchner funnel (pre warmed at 100° C.) to remove residual zinc particulates. The celite cake was washed with a small amount of additional glacial AcOH. The clear light yellow filtrate was diluted with cold water while stirring until the cloud point was reached and product crystallization began. Excess cold water was then added to precipitate the remainder of the solid product. Part of this dilution was done in 4 L Erlenmeyer flasks with magnetic stirring and part was done in a second 22 L reactor. Approximately eight 2 L portions of solution were filtered from the reactor, and approximately 18 L of quench water was used. The white solid product was collected on course glass buchner funnels, rinsed with additional de-ionized water, air suction dried for a few hours, then transferred to glass trays and air dried overnight. A final vacuum oven drying for 2.5 hrs at 0.3 mm Hg and 30° C. was carried out to give 2236 g of 3-(2-Chloro-6-fluorophenyl)-1-methyl-5-(3-methyl-4-bromo-2-thienyl)-1H-1,2,4-triazole as a white solid (theory= 2154 g), mp 118–120° C. A GC area % analysis indicated a purity of 98.1%.

EXAMPLE 6

4-Bromo-3-methyl-2-thiophenecarbonyl chloride

This example illustrates the process of Scheme III.

A. Ethyl 3-methyl-2-thiophenecarboxylate via palladium catalyzed carbonylation of 2-bromo-3-methylthiophene (Scheme III, step f)

2-Bromo-3-methylthiophene (Lancaster, 26.4 g, 0.149 mol), $Pd(OAc)_2$ (0.213 g, 0.95 mmol), 1,3-bis (diphenylphosphino) propane (0.49 g, 1.2 mmol), $Na_2CO_3$ (21.1 g, 0.20 mol), and 200 mL abs EtOH were placed into a 450 mL Hastalloy-C stirred pressure reactor, purged with $N_2$, then pressurized with 490 psig CO, and the stirring reactor was heated to 120° C. for 36 hrs. Analysis of the reaction mixture by gas chromatography showed 1.3% and 96.9% area % starting bromomethylthiophene and carbonylation product, respectively. After cooling and venting, the reactor contents were filtered and evaporated to give a light yellow oil/solid mixture. This residue was extracted with 1,2-dichloroethane and water, and the organic phase was evaporated to give an oil. Filtration of this oil to remove residual salt gave 20.7 g (81% wt. % yield) of orange oil as ethyl 3-methyl-2-thiophenecarboxylate. $^{13}C$ NMR $\{^1H\}$ $CDCl_3$: δ162.8, 145.9, 131.7, 129.9, 127.0, 60.6, 15.9, 14.4 ppm.

B. Ethyl 4-bromo-3-methyl-2-thiophenecarboxylate (Scheme III, step g)

A solution of ethyl 3-methyl-2-thiophenecarboxylate (20.0 g, 0.118 mol) and sodium hydroxide (12.3 g, 0.307 mol) in acetic acid (75 mL) was heated to 60° C. Bromine (46.9 g, 0.294 mol) was added dropwise at such a rate so as to maintain the temperature of the reaction mixture at <85 ° C. When the addition was complete, the resulting solution was stirred at 85 ° C. for 6 hours, at which time analysis by gas chromatography/mass spectrometry showed complete conversion to ethyl 4,5-dibromo-3-methyl-2-thiophenecarboxylate. The solution was allowed to cool to 50 ° C. and zinc dust (15.4 g, 0.236 mol) was added in 3 gram portions such that the exotherm was controlled to remain below 85 ° C. When the addition was completed, the resulting slurry was stirred at 85° C. for one hour. The solution was filtered hot through a small bed of celite. Water (300 mL) was added and the mixture was extracted with heptanes (300 mL). The organic phase was washed with water, then concetrated to dryness to give 26.9 g (89%) as an off white oil which slowly crystallized upon standing at ambient temperature. In a similar fashion, methyl 3-methyl-2-thiophenecarboxylate may be converted methyl-4bromo-3-methyl-2-thiophenecarboxyltate in 97% yield.

C. 4-Bromo-3-methyl-2-thiophenecarboxylic acid (Scheme III, step h)

To a solution of ethyl 4-bromo-3-methyl-2-thiophenecarboxylate (5.0 g, 0.0201 mol) in THF/MeOH/H$_2$O (4:1:1, v/v/v, 50 mL) was added NaOH (1.00 g, 0.0251 mol) and the resulting mixture was stirred at ambient temperature overnight. The mixture was acidified by adding 6 N HCl (100 mL) and water (100 mL). The resulting fine white precipitate was filtered off, washed with water and dried to give 3.80 g (86%) of 4-bromo-3-methyl-2-thiophenecarboxylic acid as a fine white solid, mp 188–189° C.

D. 4-Bromo-3-methyl-2-thiophenecarbonyl chloride (Scheme III, step i)

A slurry of 1.11 g (5 mmole) of 4-bromo-3-methyl-2-thiophenecarboxylic acid, 0.44 mL (6 mmole) of thionyl chloride, 5 drops of DMF, and 10 mL of 1,2-dichloroethane was heated at 80° C. for 1.5 h. The clear solution was cooled and concentrated on a roto-evaporator. The residue was dissolved in 5 mL of 1,2-dichloroethane and reconcentrated on a roto-evaporator to give 1.2 g of a tan solid, 97% pure (GC area). This acid chloride was used without further purification.

EXAMPLE 7

3-(2-Chloro-6-fluorophenyl)-1-methyl-5-(4-bromo-3-methyl-2-thienyl)-1H-1,2,4-triazole This example illustrates the process of Scheme II.

A. Methyl 2-chloro-6-fluoro-N-[(4-bromo-3-methyl-2-thiophene)carbonyl]benzenecarboximidothioate (Scheme II, step c)

A mixture of 0.95 g (5 mmole) of 2-chloro-6-fluorobenzenecarbothioamide, 0.5 mL (5.5 mmole) of dimethyl sulfate, and 10 mL of 1,4-dioxane was heated at 80° C. for 1 h. The clear solution was allowed to cool to room temperature, where a white precipitate formed. To the slurry was added 1.0 mL (12.5 mmole) of pyridine, followed by 1.2 g (5 mmole) of 4-bromo-3-methyl-2-thiophenecarbonyl chloride. The reaction mixture turned brown in color and a gummy insoluble material formed which made stirring difficult. The mixture was heated at 50° C. for 1.5 h. The mixture was poured onto ice and a gummy solid formed which solidified upon stirring. Stirring was continued for 1 h, and the mixture was filtered to give 1.74 g (85% wt) of a tan powder, mp 106°–109°. This material was used without further purification.

B. 3-(2-Chloro-6-fluorophenyl)-1-methyl-5-(4-bromo-3-methyl-2-thienyl)-1H-1,2,4-triazole (Scheme II, step d)

A mixture of 1.22 g (3 mmole) of methyl 2-chloro-6-fluoro-N-[(4-bromo-3-methyl-2-thiophene)carbonyl]-benzenecarboximidothioate in 5 mL of 1,4-dioxane was heated to 75° C. To the solution was added in one portion 0.24 mL (4.5 mmole) of methylhydrazine in 0.5 mL of water.

After heating here for 1.5 h, the solution was cooled and poured onto ice. The initially formed gummy solid was stirred for 1 h and filtered to give 1.03 g (89% wt) of an off-white powder. GC analysis indicated 96.4/1.7 area ratio of the desired product to off-isomer.

We claim:
1. A process for preparing a compound of the formula (1)

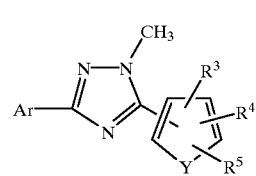

(1)

wherein

Ar is a substituted phenyl, wherein said substituted phenyl refers to a phenyl group substituted with one or more groups independently selected from halo, (C$_1$–C$_{10}$) alkyl, branched (C$_3$–C$_6$) alkyl, halo (C$_1$–C$_7$) alkyl, hydroxy (C$_1$–C$_7$) alkyl, (C$_1$–C$_7$) alkoxy, halo (C$_1$–C$_7$) alkoxy, phenoxy, phenyl, NO$_2$, OH, CN, (C$_1$–C$_4$) alkanoyl, benzoyl, (C$_1$–C$_4$) alkanoyloxy, (C$_1$–C$_4$) alkoxycarbonyl, phenoxycarbonyl, or benzoyloxy;

Y is O or S;

R$^3$ is selected from H, halo, lower alkyl, (C$_7$–C$_{21}$) straight or branched chain alkyl, hydroxy, lower alkoxy, haloalkyl, haloalkoxy, alkoxyalkyl, alkoxyalkoxy, lower alkenyl, lower alkynyl, haloalkenyl, CN, NO$_2$, COR$^6$, CO$_2$R$^6$, CON(R$^6$)$_2$, (C$_3$–C$_6$) cycloalkyl, S(O)$_m$R$^6$, —OSO$_2$R$^6$, SCN, —(CH$_2$)$_n$R$^6$, —CH=CHR$^6$, —C≡CR$^6$, —(CH$_2$)$_q$OR$^6$, —(CH$_2$)$_q$SR$^6$, — (CH$_2$)$_q$NR$^6$R$^6$, —O(CH$_2$)$_q$R$^6$, —S(CH$_2$)$_q$R$^6$, —NR$^6$(CH$_2$)$_q$R$^6$,

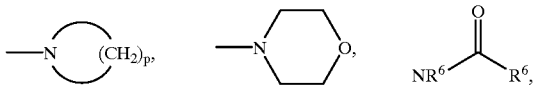

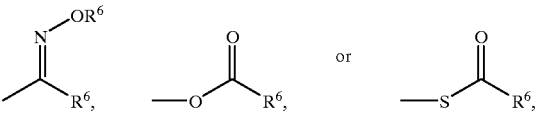

pyridyl, substituted pyridyl, isoxazolyl, substituted isoxazolyl, naphthyl, substituted naphthyl, phenyl, substituted phenyl, thienyl, substituted thienyl, pyrimidyl, substituted pyrimidyl, pyrazolyl, or substituted pyrazolyl, wherein said substituted naphthyl, substituted thienyl, substituted pyrimidyl, substituted prazolyl, substituted pyridyl, and substituted isoxaxolyl refer to the ring system substituted with one or more groups independently selected from halo, halo (C$_1$–C$_4$) alkyl, CN, NO$_2$, (C$_1$–C$_4$) alkyl, (C$_3$–C$_4$) branched alkyl, phenyl, (C$_1$–C$_4$) alkoxy, or halo (C$_1$–C$_4$) alkoxy;

R$^4$ and R$^5$ are independently H, halo, lower alkyl, lower alkoxy, haloalkyl, haloalkoxy, CN, CO$_2$R$^6$, CON(R$^6$)$_2$, or S(O)$_m$ alkyl, or if R$^4$ and R$^5$ are attached to adjacent carbon atoms, they may join to form a 5 or 6 member saturated or unsaturated carbocyclic ring which may be substituted by 1 or 2 halo, lower alkyl, lower alkoxy or haloalkyl groups;

R⁶ is H, lower alkyl, haloalkyl, lower alkenyl, lower alkynyl, phenyl, or substituted phenyl, wherein said substituted phenyl refers to a phenyl group substituted with one or more groups independently selected from halo, $(C_1-C_{10})$ alkyl, branched $(C_3-C_6)$ aklyl, halo $(C_1-C_7)$ alkyl, hydroxy $(C_1-C_7)$ alkyl, $(C_1-C_7)$ alkoxy, halo $(C_1-C_7)$ alkoxy, phenoxy, phenyl, $NO_2$, OH, CN, $(C_1-C_4)$ alkanoyl, benzoyl, $(C_1-C_4)$ alkanoyloxy, $(C_1-C_4)$ alkoxycarbonyl, phenoxycarbonyl, or benzoyloxy;

m is 0, 1, or 2;

n is 1 or 2;

p is an integer from 2 to 6; and q is 0 or 1;

which comprises the steps of:

(a) reacting a compound of formula (2)

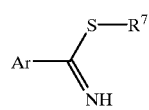

(2)

wherein Ar is as defined above and R⁷ is lower alkyl, or an acid addition salt thereof, with an acid chloride of the formula (3)

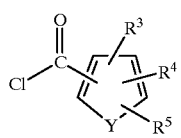

(3)

wherein Y, R³, R⁴, and R⁵ are as defined in formula (1), in an inert organic solvent the presence of an organic or inorganic base to produce an adduct-intermediate of formula (4)

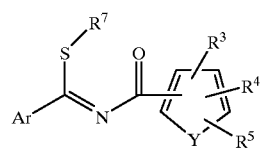

(4)

wherein Ar, Y, R³, R⁴, and R⁵ are as defined above and R⁷ is lower alkyl; and (b) with or without prior isolation of the adduct-intermediate of formula (4), reacting said adduct-intermediate with methyl hydrazine to produce the compound of formula (1).

2. A process of claim 1 wherein an acid addition salt of the reactant of formula (2) is used.

3. A process of claim 2 wherein the acid addition salt of the reactant of formula (2) is the hydroiodide or the methyl sulfate salt.

4. A process of claim 1 wherein a compound of formula (2a)

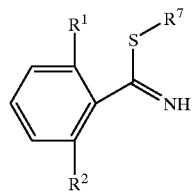

wherein

R¹ and R² are independently F or Cl, and

R⁷ is lower alkyl, or an acid addition salt thereof, is reacted with an acid chloride of the formula (3a)

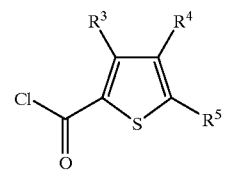

(3a)

wherein R³, R⁴ and R⁵ are independently H, CH₃, Cl, or Br to produce the adduct-intermediate of formula (4b)

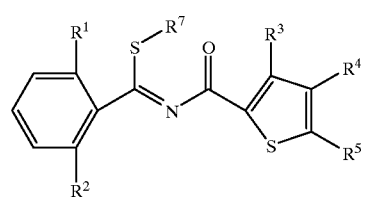

(4b)

wherein R¹, R², R³, R⁴, R⁵, and R⁷ are as defined above, and, with or without isolation of said adduct-intermediate of formula (4b), said adduct-intermediate is reacted with methyl hydrazine to produce the compound of formula (1b)

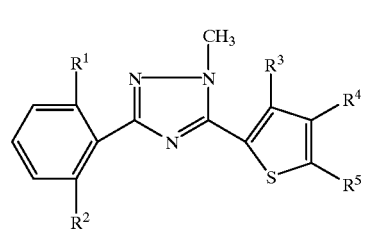

(1b)

wherein R¹, R², R³, R⁴, and R⁵ are as defined above.

5. A process of claim 4 wherein an acid addition salt of a compound of the formula

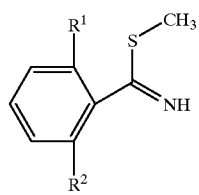

wherein $R^1$ and $R^2$ are independently F or Cl, is reacted with an acid chloride of the formula

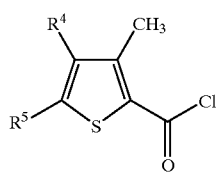

wherein $R^4$ and $R^5$ are both H or both Br, or $R^4$ is Br and $R^5$ is H, to produce an adduct intermediate of formula

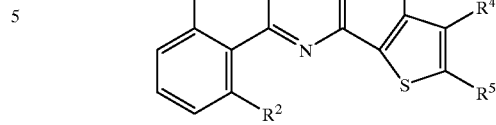

and, with or without isolation of said adduct-intermediate, said adduct-intermediate is reacted with methyl hydrazine to produce the compound of formula

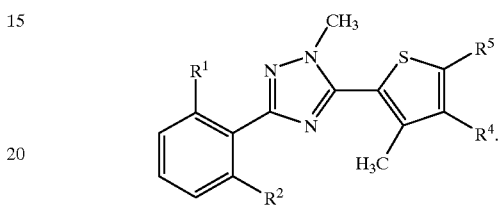

6. A process of claim 5 wherein $R^1$ is F, $R^2$ is Cl, $R^4$ is Br, and $R^5$ is H or Br.

7. A process of claim 4 wherein the adduct intermediate is reacted with methyl hydrazine in 1,4-dioxane.

* * * * *

UNITED STATES PATENT AND TRADEMARK OFFICE
CERTIFICATE OF CORRECTION

PATENT NO.    : 6,329,528 B1
DATED         : December 11, 2001
INVENTOR(S)   : Mary L. Ash et al.

It is certified that error appears in the above-identified patent and that said Letters Patent is hereby corrected as shown below:

Column 22,
Line 58, should read -- pyrazolyl, substituted pyridyl, and substituted isoxaxolyl -- rather than "prazolyl, substituted pyridyl, and substituted isoxaxolyl"

Signed and Sealed this

Fifteenth Day of July, 2003

JAMES E. ROGAN
*Director of the United States Patent and Trademark Office*